US011091410B2

(12) United States Patent
Liang et al.

(10) Patent No.: US 11,091,410 B2
(45) Date of Patent: Aug. 17, 2021

(54) MIXED OXIDE CATALYST FOR THE OXIDATIVE COUPLING OF METHANE

(71) Applicant: SABIC Global Technologies, B.V., Bergen op Zoom (NL)

(72) Inventors: Wugeng Liang, Sugar Land, TX (US); Sagar Sarsani, Sugar Land, TX (US); Aghaddin Mamedov, Sugar Land, TX (US); Hector Perez, Sugar Land, TX (US); David West, Sugar Land, TX (US); Istvan Lengyel, Sugar Land, TX (US)

( * ) Notice: Subject to any disclaimer, the term of this patent is extended or adjusted under 35 U.S.C. 154(b) by 0 days.

(21) Appl. No.: 16/491,398

(22) PCT Filed: Mar. 5, 2018

(86) PCT No.: PCT/US2018/020839
§ 371 (c)(1),
(2) Date: Sep. 5, 2019

(87) PCT Pub. No.: WO2018/164983
PCT Pub. Date: Sep. 13, 2018

(65) Prior Publication Data
US 2020/0017424 A1    Jan. 16, 2020

Related U.S. Application Data

(60) Provisional application No. 62/467,587, filed on Mar. 6, 2017.

(51) Int. Cl.
| | | |
|---|---|---|
| *C07C 2/84* | (2006.01) | |
| *B01J 23/00* | (2006.01) | |
| *B01J 23/10* | (2006.01) | |
| *B01J 23/30* | (2006.01) | |
| *B01J 35/02* | (2006.01) | |
| *B01J 37/00* | (2006.01) | |
| *B01J 37/04* | (2006.01) | |
| *B01J 37/08* | (2006.01) | |

(52) U.S. Cl.
CPC ............. *C07C 2/84* (2013.01); *B01J 23/002* (2013.01); *B01J 23/10* (2013.01); *B01J 23/30* (2013.01); *B01J 35/023* (2013.01); *B01J 37/0036* (2013.01); *B01J 37/04* (2013.01); *B01J 37/08* (2013.01); *B01J 2523/24* (2013.01); *B01J 2523/3706* (2013.01); *B01J 2523/3712* (2013.01); *B01J 2523/3725* (2013.01); *B01J 2523/3737* (2013.01); *B01J 2523/3775* (2013.01); *B01J 2523/3787* (2013.01); *B01J 2523/69* (2013.01); *C07C 2523/02* (2013.01); *C07C 2523/10* (2013.01); *C07C 2523/30* (2013.01)

(58) Field of Classification Search
CPC . B01J 23/002; B01J 23/10; B01J 23/30; B01J 2523/24; B01J 2523/3706; B01J 2523/3712; B01J 2523/3725; B01J 2523/3737; B01J 2523/3775; B01J 2523/3787; B01J 2523/69; C07C 2/84; C07C 2523/02; C07C 2523/10; C07C 2523/30
USPC ........................................ 502/302, 305–355
See application file for complete search history.

(56) References Cited

U.S. PATENT DOCUMENTS

| | | | | |
|---|---|---|---|---|
| 3,885,020 | A * | 5/1975 | Whelan ................ | B01D 53/945 423/245.3 |
| 3,947,380 | A * | 3/1976 | Whelan .................... | B01J 23/86 502/302 |
| 4,997,802 | A * | 3/1991 | Matsuura ................. | B01J 23/04 502/302 |
| 5,024,984 | A * | 6/1991 | Kaminsky ................ | B01J 23/14 502/302 |
| 5,591,315 | A * | 1/1997 | Mazanec ............ | B01D 67/0041 205/462 |
| 5,728,643 | A * | 3/1998 | Naitoh ............... | B01D 53/9413 502/302 |
| 10,669,218 | B2 * | 6/2020 | Mamedov ................. | C07C 5/48 |
| 2008/0281136 | A1* | 11/2008 | Bagherzadeh ......... | B01J 23/002 585/310 |
| 2009/0253574 | A1* | 10/2009 | Tanaka ................... | B01J 23/894 502/303 |
| 2015/0073192 | A1* | 3/2015 | Cizeron ................... | B01J 27/16 585/500 |
| 2015/0217275 | A1* | 8/2015 | Ito ........................... | B01J 23/10 502/303 |
| 2015/0314267 | A1* | 11/2015 | Schammel .............. | B01J 37/03 585/500 |
| 2017/0014807 | A1* | 1/2017 | Liang ....................... | C07C 2/84 |
| 2020/0298209 | A1* | 9/2020 | Liang .................. | B01J 35/1061 |

* cited by examiner

*Primary Examiner* — Patricia L. Hailey
(74) *Attorney, Agent, or Firm* — Sheri Higgins; Sheri Higgins Law, PLLC

(57) ABSTRACT

A mixed oxide catalyst for the oxidative coupling of methane can include a catalyst with the formula $A_aB_bC_cD_dO_x$, wherein: element A is selected from alkaline earth metals; elements B and C are selected from rare earth metals, and wherein elements B and C are different rare earth metals; the oxide of at least one of A, B, C, and D has basic properties; the oxide of at least one of A, B, C, and D has redox properties; and elements A, B, C, and D are selected to create a synergistic effect whereby the catalytic material provides a methane conversion of greater than or equal to 15% and a $C_2^+$ selectivity of greater than or equal to 70%. Systems and methods can include contacting the catalyst with methane and oxygen and purifying or collecting $C_2^+$ products.

19 Claims, No Drawings

MIXED OXIDE CATALYST FOR THE OXIDATIVE COUPLING OF METHANE

TECHNICAL FIELD

Oxidative coupling of methane (OCM) is a process whereby methane is converted into products, such as ethane and ethylene. A catalyst can be used in the presence of oxygen for the OCM reaction.

DETAILED DESCRIPTION OF THE INVENTION

Ethylene is crucial in the manufacture of many products, including food packaging, medical devices, lubricants, and engine coolants. Due to the crucial role ethylene plays in the production of these products, it is estimated that the production of ethylene is $160 billion per year. Heterogeneous catalysts can be used to convert methane into other products, such as ethane and ethylene, using an oxidative coupling of methane (OCM) process. In the reaction, methane ($CH_4$) is activated heterogeneously on the catalyst surface, forming methyl free radicals, which then couple in the gas phase to form ethane ($C_2H_6$). The ethane can then subsequently undergo dehydrogenation to form ethylene ($C_2H_4$). The OCM of methane to ethylene is shown in the equation below.

$$2CH_4 + O_2 \rightarrow C_2H_4 + 2H_2O \quad (Eq. 1)$$

However, there are many challenges in OCM to produce desirable products. For example, the yield of the desired $C_2^+$ products can be reduced by non-selective reactions of the methyl radicals with the surface of the catalyst and oxygen in the gas phase, which produce undesirable products, such as carbon monoxide and carbon dioxide. Methane activation can be difficult because of its thermodynamic stability with a noble-gas-like electronic configuration. The tetrahedral arrangement of strong C-H bonds (435 kJ/mol) offer no functional group, magnetic moments, or polar distributions to undergo chemical attack. This makes methane less reactive than nearly all of its conversion products, which severely limits efficient utilization of natural gas, the world's most abundant petrochemical resource, as a source for ethylene production. Moreover, the reaction is exothermic, which creates challenges in reactor design to deal with efficient heat transfer.

Additionally, many catalysts fail to produce sufficient quantities of the desired products, while also being economically unfeasible. For the OCM reaction to occur, reactant methane needs to be activated into the methyl free radicals on the surface of the catalyst. In order to activate methane, the catalyst needs to possess basic properties. The reduced catalyst surface must then be re-oxidized back to its initial state in order for the reaction to continue. In order for re-oxidation to occur, the catalyst needs to possess redox properties. Thus, the high performance catalyst should possess both basic and redox properties. However, high basic properties lead to increased selectivity of $C_2^+$ products, but may reduce the stability of the catalyst; whereas, high redox properties may stabilize catalyst performance, but may reduce selectivity of $C_2^+$ products. Therefore, there is a continuing need and ongoing industry concern for improved catalysts that can be used to produce $C_2^+$ products by oxidative coupling of methane.

It has been discovered that a catalyst can be used for the OCM to form $C_2^+$ products. The catalyst possesses basic and redox properties in a ratio whereby catalyst activity is increased. It has also been unexpectedly discovered that the materials making up the catalyst create a synergistic effect that provides an increased methane conversion and increased selectivity of $C_2^+$ products.

As used herein, "$C_2$" refers to a hydrocarbon (i.e., a compound consisting of carbon and hydrogen atoms) having only two carbon atoms, for example ethane and ethylene. As used herein, the term "conversion" means the mole fraction (i.e., the percent) of a reactant converted to a product or products. As used herein, the term "selectivity" refers to the percent of converted reactant that went to a specified product (e.g., $C_2^+$ selectivity is the percent of converted methane that formed $C_2$ and higher hydrocarbons).

It is to be understood that any discussion of the various embodiments is intended to apply to the compositions, systems, and methods.

According to certain embodiments, a catalytic material for oxidative coupling of methane comprises: a catalyst with the formula $A_aB_bC_cD_dO_x$, wherein: element A is selected from alkaline earth metals; elements B and C are selected from rare earth metals, and wherein B and C are different rare earth metals; the oxide of at least one of A, B, C, and D has basic properties; the oxide of at least one of A, B, C, and D has redox properties; and elements A, B, C, and D are selected to create a synergistic effect whereby the catalytic material provides a methane conversion of greater than or equal to 15% and a $C_2^+$ selectivity of greater than or equal to 70%.

According to certain other embodiments, a system for oxidative coupling of methane comprises: a source of methane; a source of oxygen; the catalytic material, wherein the catalytic material produces ethane, ethylene, or combinations thereof; and a device for collecting or purifying the ethane, ethylene, or combinations thereof.

According to certain other embodiments, a method for the oxidative coupling of methane comprises: providing a source of methane; providing a source of oxygen; contacting the source of methane and the source of oxygen with the catalytic material, wherein the catalytic material produces ethane, ethylene, or combinations thereof after contact with the source of methane and the source of oxygen; and collecting or purifying the ethane, ethylene, or combinations thereof.

The catalyst can lower the transition state, increases the reaction rate, increase conversion of reactants, increase selectivity for a certain product, or combinations thereof, under operating conditions. According to certain embodiments, the catalyst is an OCM active catalyst and increases the rate of the OCM reaction relative to an uncatalyzed OCM reaction.

The catalyst has the general formula $A_aB_bC_cD_dO_x$, wherein: $a = 1.0$; $b$, $c$, and $d$ are each in the range from about 0.01 to about 10; and $x$ is a number selected to balance the oxidation state of elements A, B, C, and D. It is to be understood that the general formula is meant to include the oxides of the elements A, B, C, and D and not just an oxide of D. According to certain embodiments, each of the elements A, B, C, and D is an oxide—and can be expressed as $A_aO_xB_bO_xC_cO_xD_dO_x$. According to certain other embodiments, some of the elements A, B, C, and D combine to form compound oxides. For example, elements A and B can form a compound oxide of $A_aB_bO_x$ (e.g., strontium cerium oxide); or elements A, B, and C can form a compound oxide of $A_aB_bC_cO_x$ (e.g., strontium cerium ytterbium oxide). The formation of compound oxides can occur during formation of the catalyst—depending on the specific elements selected.

Element A is selected from alkaline earth metals. According to certain embodiments, A is selected from the group consisting of magnesium, calcium, strontium, and barium. Elements B and C are selected from rare earth metals, wherein B and C are different rare earth metals. According to certain embodiments, B and C are selected from the group consisting of cerium (Ce), ytterbium (Yb), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), terbium (Tb), scandium (Sc), yttrium (Y), and thulium (Tm). Element D can be selected from the group consisting of a transition metal, a post-transition metal, a metalloid, and a rare earth metal, wherein if D is selected from a rare earth metal, then D is a different rare earth metal from B and C. According to certain embodiments, D is selected from the group consisting of manganese, tungsten, bismuth, antimony, and a rare earth metal (e.g., erbium, samarium, lanthanum, and neodymium).

As used herein, a "metal element" is any element, except hydrogen, selected from Groups 1 through 12 of the periodic table, lanthanides, actinides, aluminum (Al), gallium (Ga), indium (In), tin (Sn), thallium (Tl), lead (Pb), and bismuth (Bi). Metal elements include metal elements in their elemental form as well as metal elements in an oxidized or reduced state, for example, when a metal element is combined with other elements in the form of compounds comprising metal elements. For example, metal elements can be in the form of hydrates, salts, oxides, nitrates, carbonates, as well as various polymorphs thereof, and the like. As used herein, an "alkaline earth metal" is an element from Group 2 of the periodic table and includes beryllium (Be), magnesium (Mg), calcium (Ca), strontium (Sr), barium (Ba), and radium (Ra). As used herein, a "rare earth metal" is one of the fifteen lanthanides as well as scandium and yttrium, and includes cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), and yttrium (Y). As used herein, a "transition metal" is an element from Groups 4 through 12 of the periodic table as well as scandium (Sc) and yttrium (Y) from Group 3. As used herein, a "post-transition metal" is an element located between transition metals and metalloids, and includes gallium (Ga), indium (In), thallium (Tl), tin (Sn), lead (Pb), and bismuth (Bi). A "metalloid" generally refers to the elements boron (B), silicon (Si), germanium (Ge), arsenic (As), antimony (Sb), and tellurium (Te).

The oxide of at least one of A, B, C, and D has basic properties. The oxide of at least one of A, B, C, and D has redox properties. The oxide of more than one, or all, of elements A, B, C, and D can include basic properties. The oxide of more than one of elements A, B, C, and D can include redox properties. One or more of elements A, B, C, and D can also possess both basic and redox properties.

Any of the oxides of A, B, C, and D can have different oxidation states when forming the oxide. The catalyst can be a mixture of different metal oxides and/or metal oxides having different oxidation states, to form a catalyst having two or more phases. Some of the oxides can undergo a change in oxidation state during the oxidative coupling of methane reaction. It may be that an oxide of one of the elements having basic properties, but not redox properties, can have catalytic properties without undergoing a change in oxidation state. However, the oxide of one of the elements having redox or both basic and redox properties can undergo a change in oxidation state during the reaction. For example, cerium (IV) oxide has a higher oxidation state compared to cerium (III) oxide; and thus, will be reduced by methane to form cerium (III) oxide, which in turn, becomes oxidized by oxygen to form cerium (IV) oxide. Thus, the oxidative coupling reaction can continue.

According to certain embodiments, elements A, B, C, and D are selected to create a synergistic effect whereby the catalytic material provides a desired methane conversion and desired $C_2^+$ selectivity. The concentration (e.g., the volume or molar ratios) of elements A, B, C, and D can vary. The concentration can be selected to provide a desired methane conversion and $C_2^+$ selectivity.

The catalytic material can be combined with a support, binder and/or diluent material. The support and binder can be selected from any suitable material known to those skilled in the art. The diluents can be selected from bulk materials, nano materials (e.g., nanowires, nanorods, nanoparticles, etc.), and combinations thereof.

The catalytic material can be in any suitable form including, but not limited to, powder, tablet, or extruded form. Powder forms can be customized by selecting appropriate particle size distributions that provide a desired $C_2^+$ selectivity and methane conversion. The catalyst can also have a variety of shapes including, but not limited to, cylinder, ring, flat sheet, multi-lobe cylinder, wagon wheel, etc. The catalyst can also have a variety of dimensions—depending in part, on the type of reactor used and the scale of the operation. One of ordinary skill in the art will be able to select the appropriate dimensions for the catalyst.

It is also desirable to provide formed catalysts having a uniform porosity. The porosity of a material is the void fraction or percent of empty spaces within a material. For example, the porosity of the formed catalyst can directly impact the efficiency of the catalyst by providing accessibility of the reactants to the catalysts surfaces where the reaction of interest is catalyzed. Variances of the porosity of the catalyst, either within a single formed catalyst particle, or between different catalyst particles, can impact the overall efficiency of the catalytic material, for example, by providing regions of low activity and regions of high activity. The regions with different activity can lead to additional issues, such as thermal non-uniformity in catalyst particles or catalyst beds. Moreover, the relative porosity of a catalyst particle can also directly impact its structural characteristics, such as crush strength, leading to catalyst particles that have relatively lower crush strength in one portion of the particle or in one particle relative to another. This difference in structural properties can again, impact catalytic processes by altering handling and processing ability, generation of fines, and other issues. According to certain embodiments, the catalytic material has a uniform porosity, which can be provided, at least in part, through the use of powdered compositions having uniform particle size distributions. The porosity of a tablet or extruded form can also be selected to provide a desired $C_2^+$ selectivity and methane conversion. According to certain embodiments, the porosity is in the range of about 10% to about 80%.

According to certain embodiments, the desired methane conversion is greater than or equal to 15% or 18%. According to certain embodiments, the $C_2^+$ selectivity is greater than or equal to 70%, 75%, or 80%. The elements A, B, C, and D and their concentrations can be selected to provide the stated methane conversion and $C_2^+$ selectivity.

The catalytic material, including a support, binder, or diluent, can be made by a variety of processes known to those skilled in the art. Examples of suitable processes include, but are not limited to, tableting and extrusion.

It has been discovered that the catalytic material according to the embodiments is stable for a much longer period of time compared to other catalytic materials. This long stability can greatly reduce cost and time from having to switch the catalyst in a system at more frequent time intervals. According to certain embodiments, the catalytic material is stable for at least 6 months, more preferably a year, at operating temperatures and pressures. According to certain embodiments, elements A, B, C, and D are selected such that the catalytic material is thermally and chemically stable for the specified period of time under operating conditions. The operating temperature can be in the range of about 572° F. (300° C.) to about 2,372° F. (1,300° C.) or in the range of about 932° F. (500° C.) to about 2,012° F. (1,100° C.). The catalytic material can be thermally stable at a temperature in the range of about 572° F. (300° C.) to about 2,372° F. (1,300° C.) or in the range of about 932° F. (500° C.) to about 2,012° F. (1,100° C.). The catalytic material can be stable at a pressure in the range of about 1 bar to about 100 bars or in the range of about 1 bar to about 10 bars.

A system for oxidative coupling of methane can include a source of methane, a source of oxygen, the catalytic material, and a device for collecting the ethane, ethylene, or combinations thereof.

The system can include feed and product streams for $C_2$ production. A first feed stream can be the source of methane, and a second feed stream can be the source of oxygen. The source of methane can include natural gas, associated gas, and shale gas. The source of oxygen can include air, oxygen enriched air, pure oxygen, oxygen diluted with nitrogen (or another inert gas), or oxygen diluted with carbon dioxide ($CO_2$). A first product stream can include water and hydrogen gas, and a second product stream can include ethane ($C_2H_6$), ethylene ($C_2H_4$), and other reaction products.

Any of the feeds or products can be separated, condensed, and/or recycled back into a given feed or product stream. For example, hydrogen gas and any unreacted steam from the second product stream can be separated, collected, and stored or recycled back into the feed stream. By way of another example, the products from the product streams can be flowed through one or more distillation columns or other separators to separate $C_2$ products from other reaction products.

The ratio of methane to oxygen from the product stream(s) can vary. The $C_2^+$ selectivity, methane conversion, and percent yield of $C_2$ products can also vary depending on the ratio of methane to oxygen for a particular catalytic material under operating conditions. According to certain embodiments, the ratio of methane to oxygen is selected to provide a percent yield of the ethane, ethylene, or combinations thereof that is greater than or equal to 10%, preferably greater than or equal to 15%. According to certain other embodiments, the ratio of methane to oxygen is in the range of about 2:1 to about 10:1. The ratio of methane to oxygen as well as the selection and concentration of A, B, C, and D can be selected to provide an increased percent yield of $C_2$ products. It may be desirable to produce more ethylene than ethane. Therefore, according to certain embodiments, the ratio of methane to oxygen as well as the selection and concentration of elements A, B, C, and D are selected to provide an increased percent yield of ethylene.

Methods for the oxidative coupling of methane can include providing a source of methane, providing a source of oxygen, contacting the source of methane and the source of oxygen with the catalytic material, and collecting the ethane, ethylene, or combinations thereof.

The operating temperature for the OCM reaction can be in the range of about 572° F. (300° C.) to about 2,372° F. (1,300° C.) or in the range of about 932° F. (500° C.) to about 2,012° F. (1,100° C.). The operating pressure can be in the range of about 1 bar to about 100 bars or in the range of about 1 bar to about 10 bars. The gas hourly space velocity (GHSV) for the OCM reaction can range from about 500 $hr^{-1}$ to 5,000,000 $hr^{-1}$, or from 5000 $hr^{-1}$ to 1,000,000 $hr^{-1}$.

EXAMPLES

To facilitate a better understanding of the present invention, the following examples of certain aspects of preferred embodiments are given. The following examples are not the only examples that could be given according to the present invention and are not intended to limit the scope of the invention.

Catalysts having the general formula $A_aB_bC_cD_dO_x$ were prepared according to the following method. Reference catalysts having the general formula $A_aB_bC_cO_x$ were also prepared using the same method. The catalysts were formed by placing a known amount of the nitrates of elements A, B, C, and (optionally) D in a beaker and dissolved with 25 milliliters (mL) of deionized water to obtain the specific oxide weight percent concentration shown in the tables below. By way of example, to obtain 10 grams (g) of the reference catalyst in Table 1, 4.23 g of $Sr(NO_3)_2$, 7.82 g of $Ce(NO_3)_3.6H_2O$, and 0.90 g of $Yb(NO_3)_3.5H_2O$ were added to a beaker. Stirring was performed until the substances dissolved. The mixtures were then dried at a temperature of about 125° C. for at least 8 hours. The cakes were then transferred to a porcelain dish and placed in a heating oven for calcination at a temperature of 900° C. for 6 hours. The solid catalysts were crushed to powder and sieved to form a product having a particle size between 20 to 50 mesh. 20 milligrams (mg) of the catalysts were then loaded into a 2.3 millimeter (mm) inner diameter quartz tube reactor. A feed stream of a mixture of methane and oxygen at a methane to oxygen ratio of 7.4:1 was flowed over the catalyst at a flow rate of 40 standard cubic centimeters per minute (sccm). Catalyst performances were obtained by varying the reactor temperatures. The methane conversion, oxygen conversion, and $C_2^+$ selectivity were measured using an Agilent 7890 gas chromatograph with a thermal conductivity detector and a flame ionization detector.

TABLE 1

| Catalyst # | Catalyst Composition | $CH_4$ Conversion (%) | $O_2$ Conversion (%) | $C_2^+$ Selectivity (%) | Temperature (° C.) |
|---|---|---|---|---|---|
| Reference | $Sr_{1.0}Ce_{0.9}Yb_{0.1}O_x$ | 18.0 | 99.0 | 77.4 | 750.0 |
| 1 | $Sr_{1.0}Ce_{0.9}Yb_{0.1}Er_{0.1}O_x$ | 19.3 | 94.7 | 81.3 | 775.0 |
| 2 | $Sr_{1.0}Ce_{0.9}Yb_{0.1}Sm_{0.1}O_x$ | 16.9 | 100.0 | 74.4 | 750.0 |
| 3 | $Sr_{1.0}Ce_{0.9}Yb_{0.1}Sm_{0.2}O_x$ | 20.1 | 100.0 | 80.0 | 750.0 |
| 4 | $Sr_{1.0}Ce_{0.9}Yb_{0.1}Sm_{0.5}O_x$ | 18.6 | 100.0 | 78.9 | 700.0 |
| 5 | $Sr_{1.0}Ce_{0.9}Yb_{0.1}La_{0.1}O_x$ | 17.3 | 97.8 | 74.3 | 775.0 |

TABLE 1-continued

| Catalyst # | Catalyst Composition | CH$_4$ Conversion (%) | O$_2$ Conversion (%) | C$_2^+$ Selectivity (%) | Temperature (° C.) |
|---|---|---|---|---|---|
| 6 | Sr$_{1.0}$Ce$_{0.9}$Yb$_{0.1}$La$_{0.2}$O$_x$ | 16.9 | 100.0 | 74.5 | 700.0 |
| 7 | Sr$_{1.0}$Ce$_{0.9}$Yb$_{0.1}$La$_{0.5}$O$_x$ | 19.5 | 100.0 | 80.2 | 700.0 |
| 8 | Sr$_{1.0}$Ce$_{0.9}$Yb$_{0.1}$Nd$_{0.1}$O$_x$ | 19.0 | 99.9 | 79.4 | 750.0 |
| 9 | Sr$_{1.0}$Ce$_{0.9}$Yb$_{0.1}$Nd$_{0.2}$O$_x$ | 18.8 | 100.0 | 78.5 | 725.0 |
| 10 | Sr$_{1.0}$Ce$_{0.9}$Yb$_{0.1}$Nd$_{0.5}$O$_x$ | 18.7 | 100.0 | 78.9 | 725.0 |
| 11 | Sr$_{1.0}$Ce$_{0.9}$Yb$_{0.1}$W$_{0.05}$O$_x$ | 18.7 | 99.5 | 76.1 | 750.0 |
| 12 | Sr$_{1.0}$Ce$_{0.9}$Yb$_{0.1}$W$_{0.1}$O$_x$ | 16.3 | 100.0 | 71.4 | 700.0 |
| 13 | Sr$_{1.0}$Ce$_{0.9}$Yb$_{0.1}$W$_{0.2}$O$_x$ | 18.3 | 100.0 | 78.5 | 700.0 |

As can be seen from the data in Table 1, at least one of the catalysts in the groups 2-4, 5-7, 8-10, and 11-13 performed better than the reference catalyst that did not include D$_d$O$_x$. This indicates that a synergistic effect is created with the addition of element D. At least one of the catalysts from these groups provided a higher methane conversion and C$_2^+$ selectivity. As can also be seen, the concentration of D$_d$O$_x$ can be selected to provide better results. Of the D elements, samarium (Sm), at a concentration of 0.2, produced the highest methane conversion, while erbium (Er), at a concentration of 0.1, produced the highest C$_2^+$ selectivity.

In addition to the impact on C$_2^+$ selectivity and methane conversion, the selection of element D can also have an impact on the catalyst activity. The catalyst activity is indicated by the temperature at which the O$_2$ conversion reaches 90% or higher, as shown in the last column in Table 1. As can be seen from the data in Table 1, at least one of the catalysts in the groups 2-4, 5-7, 8-10, and 11-13 showed higher activity than the reference catalyst that did not include D$_d$O$_x$. Of the D elements, samarium (Sm), at a concentration of 0.5, due to its higher activity, the reactor temperature can be lowered by 50° C. to achieve the same O$_2$ conversion. The same level of activity can also be achieved by La 0.2, La 0.5, W 0.1 and W 0.2. Catalyst #7, with La 0.5, demonstrated high activity, high C$_2^+$ selectivity, and high methane conversion.

These results indicate that not only can the A, B, C, D elements be selected, but also that the concentration of each element can be selected to make the catalyst have balanced basicity and redox properties, such that high activity, high selectivity, and stable performance can be obtained.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention.

As used herein, the words "comprise," "have," "include," and all grammatical variations thereof are each intended to have an open, non-limiting meaning that does not exclude additional elements or steps. While compositions and methods are described in terms of "comprising," "containing," or "including" various components or steps, the compositions and methods also can "consist essentially of" or "consist of" the various components and steps. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

What is claimed is:

1. A catalytic material for oxidative coupling of methane comprising:
   a catalyst with the formula A$_a$B$_b$C$_c$D$_d$O$_x$, wherein:
   element A is selected from alkaline earth metals;
   elements B and C are selected from rare earth metals, and wherein elements B and C are different rare earth metals;
   the oxide of at least one of A, B, C, and D has basic properties;
   the oxide of at least one of A, B, C, and D has redox properties;
   $a$=1.0; $b$, $c$, and $d$ are each in the range from about 0.01 to about 10; and $x$ is a number selected to balance the oxidation state of D; and
   elements A, B, C, and D are selected to create a synergistic effect whereby the catalytic material provides a methane conversion of greater than or equal to 15% and a C$_2^+$ selectivity of greater than or equal to 70%.

2. The catalytic material according to claim 1, wherein element A is selected from the group consisting of magnesium, calcium, strontium, and barium.

3. The catalytic material according to claim 1, wherein elements B and C are selected from the group consisting of cerium, ytterbium, dysprosium, erbium, europium, gadolinium, holmium, lanthanum, lutetium, neodymium, praseodymium, promethium, samarium, terbium, scandium, yttrium, and thulium.

4. The catalytic material according to claim 1, wherein element D is selected from the group consisting of a transition metal, a post-transition metal, a metalloid, and a rare earth metal, wherein if D is selected from a rare earth metal, then D is a different rare earth metal from B and C.

5. The catalytic material according to claim 4, wherein element D is selected from the group consisting of manganese, tungsten, bismuth, antimony, and a rare earth metal.

6. The catalytic material according to claim 1, wherein elements A, B, C, and D are selected to provide a methane conversion of greater than or equal to 18% and a C$_2^+$ selectivity of greater than or equal to 80%.

7. The catalytic material according to claim 1, wherein the concentration of elements A, B, C, and D are selected to provide a methane conversion of greater than or equal to 15% and a $C_2^+$ selectivity of greater than or equal to 70%.

8. The catalytic material according to claim 1, whereby the catalytic material provides a methane conversion of greater than or equal to 18% and a $C_2^+$ selectivity of greater than or equal to 75%.

9. The catalytic material according to claim 1, wherein the catalyst further comprises a support, binder, diluent material, or combinations thereof.

10. The catalytic material according to claim 1, wherein the catalyst is thermally stable at a temperature in the range of about 300° C. to about 1,300° C.

11. The catalytic material according to claim 1, wherein the catalyst is thermally stable at a temperature in the range of about 500° C. to 1,100° C.

12. The catalytic material according to claim 1, wherein the catalyst is stable for at least 6 months at a temperature in the range of about 300° C. to about 1,300° C. and a pressure in the range of about 1 bar to about 100 bars.

13. The catalytic material according to claim 1, wherein the catalyst is stable for at least 1 year at a temperature in the range of about 300° C. to about 1,300° C. and a pressure in the range of about 1 bar to about 100 bars.

14. A system for oxidative coupling of methane comprising:
   a source of methane;
   a source of oxygen;
   a catalytic material, wherein the catalytic material comprises a catalyst with the formula $A_aB_bC_cD_dO_x$, and wherein:
      element A is selected from alkaline earth metals;
      elements B and C are selected from rare earth metals, and wherein B and C are different rare earth metals;
      the oxide of at least one of A, B, C, and D has basic properties;
      the oxide of at least one of A, B, C, and D has redox properties;
      $a$=1.0; $b$, $c$, and $d$ are each in the range from about 0.01 to about 10; and $x$ is a number selected to balance the oxidation state D; and
      elements A, B, C, and D are selected to create a synergistic effect whereby the catalytic material provides a methane conversion of greater than or equal to 15% and a $C_2^+$ selectivity of greater than or equal to 70%, and
   wherein the catalytic material produces ethane, ethylene, or combinations thereof; and a device for collecting or purifying the ethane, ethylene, or combinations thereof.

15. The system according to claim 14, wherein element D is selected from the group consisting of a transition metal, a post-transition metal, a metalloid, and a rare earth metal, wherein if D is selected from a rare earth metal, then D is a different rare earth metal from B and C.

16. The system according to claim 14, wherein the ratio of methane to oxygen is in the range of about 2:1 to about 10:1.

17. A method for the oxidative coupling of methane comprising:
   providing a source of methane;
   providing a source of oxygen;
   contacting the source of methane and the source of oxygen with a catalytic material, wherein the catalytic material comprises a catalyst with the formula $A_aB_bC_cD_dO_x$, and wherein:
      element A is selected from alkaline earth metals;
      elements B and C are selected from rare earth metals, and wherein B and C are different rare earth metals;
      the oxide of at least one of A, B, C, and D has basic properties;
      the oxide of at least one of A, B, C, and D has redox properties;
      $a$=1.0; $b$, $c$, and $d$ are each in the range from about 0.01 to about 10; and $x$ is a number selected to balance the oxidation state of D; and
      elements A, B, C, and D are selected to create a synergistic effect whereby the catalytic material provides a methane conversion of greater than or equal to 15% and a $C_2^+$ selectivity of greater than or equal to 70%, and
   wherein the catalytic material produces ethane, ethylene, or combinations thereof after contact with the source of methane and the source of oxygen; and
   collecting or purifying the ethane, ethylene, or combinations thereof.

18. The method according to claim 17, wherein element D is selected from the group consisting of a transition metal, a post-transition metal, a metalloid, and a rare earth metal, wherein if D is selected from a rare earth metal, then D is a different rare earth metal from B and C.

19. The method according to claim 17, wherein the ratio of methane to oxygen is in the range of about 2:1 to about 10:1.

* * * * *